(12) United States Patent
Albeck et al.

(10) Patent No.: US 6,472,381 B1
(45) Date of Patent: Oct. 29, 2002

(54) METHOD OF TREATING PSORIASIS

(75) Inventors: Michael Albeck, Ramat Gan;
Benjamin Sredni, Kfar Saba, both of (IL)

(73) Assignee: Biomas Inc., Tel Aviv (IL)

( * ) Notice: Subject to any disclaimer, the term of this patent is extended or adjusted under 35 U.S.C. 154(b) by 0 days.

(21) Appl. No.: 09/975,792

(22) Filed: Oct. 12, 2001

(51) Int. Cl.⁷ .................. A61K 31/615; A61K 31/605; A61K 31/28
(52) U.S. Cl. .................. 514/162; 514/164; 514/492
(58) Field of Search .................. 514/492, 162, 514/164

(56) References Cited

U.S. PATENT DOCUMENTS 4,761,490 A * 8/1988 Albeck et al. .............. 549/347

* cited by examiner

*Primary Examiner*—Raymond Henley, III
(74) *Attorney, Agent, or Firm*—Hedman & Costigan, P.C.

(57) ABSTRACT

The invention comprises the administration of an effective amount of a tellurium compound to a patients who is afflicted with psoriasis. The tellurium compound is administered either systemically or topically to one who is afflicted with psoriasis in an amount which is effective to alleviate the symptoms of psoriasis.

10 Claims, No Drawings

METHOD OF TREATING PSORIASIS

BACKGROUND OF THE INVENTION

Psoriasis is a well known condition which affects the skin of affected patients. The disease manifests itself as chronic, recurring silvery papules, scaling papules and plaques of various sizes. The condition may consist of one or two lesions or may be a widespread dermatosis with disabling arthritis or exfoliation. The cause is not known. Treatment in the prior art has comprised the use of lubricants, keratolytics, and topical corticosteroids. In severe disabling psoriasis, methotrexate may be used or PUVA (psoralens and high intensity ultraviolet light) masy be used.

The applicant has discovered that the use of a tellurium compound will alleviate the symptoms of psoriasis.

SUMMARY OF THE INVENTION

The invention comprises the administration of an effective amount of a tellurium compound to a patients who is afflicted with psoriasis. The tellurium compound is administered either systemically or topically to one who is afflicted with psoriasis in an amount which is effective to alleviate the symptoms of psoriasis.

Accordingly it is a primary object of the invention to provide a method for the treatment of psoriasis which uses a tellurium based compound.

It is also an object of the invention to provide a method of treating psoriasis which is based on the systemic dosing of a tellurium compound.

It is also an object of the invention to provide a method of treating psoriasis which is based on the topical application of a tellurium compound.

It is also an object of this invention to provide a novel composition of a keratolytic agent and a tellurium compound.

These and other objects of the invention will become apparent from a review of the appended specification.

DETAILED DESCRIPTION OF THE INVENTION

The tellurium compounds for use in the invention include those of the formula:

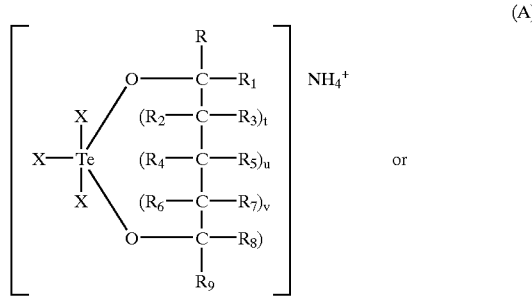

(A)

or

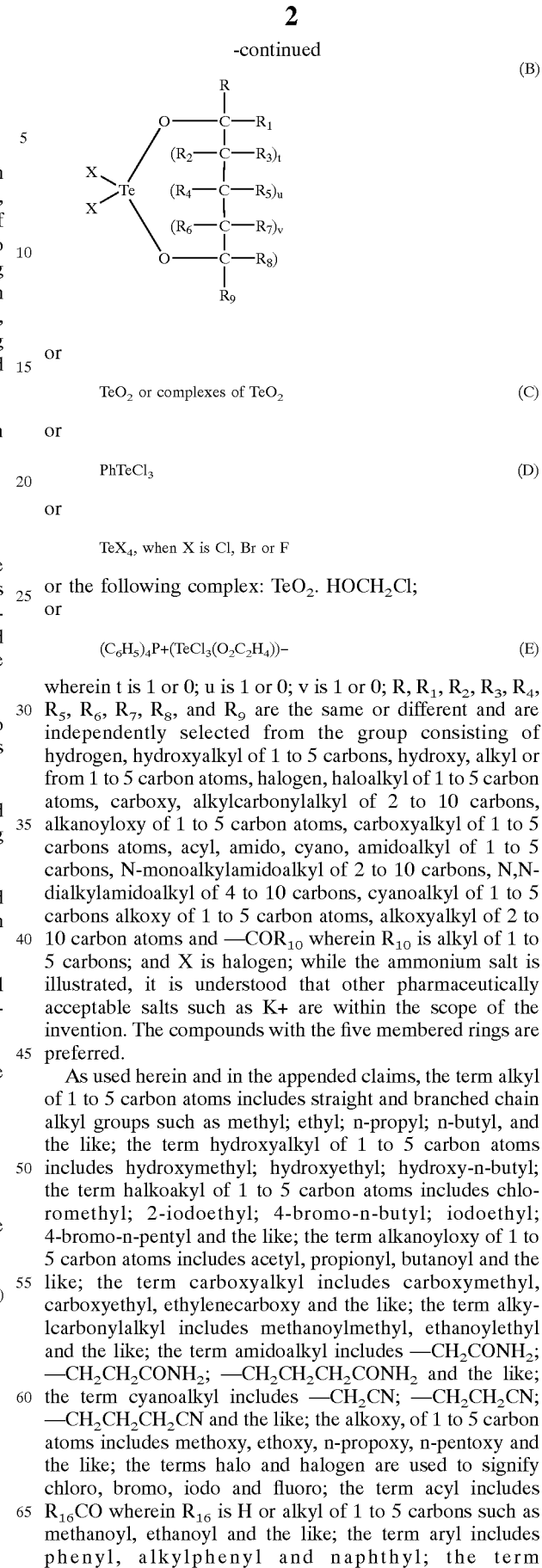

(B)

or

TeO$_2$ or complexes of TeO$_2$     (C)

or

PhTeCl$_3$     (D)

or

TeX$_4$, when X is Cl, Br or F or the following complex: TeO$_2$·HOCH$_2$Cl;

or $(C_6H_5)_4P+(TeCl_3(O_2C_2H_4))-$     (E)

wherein t is 1 or 0; u is 1 or 0; v is 1 or 0; R, $R_1$, $R_2$, $R_3$, $R_4$, $R_5$, $R_6$, $R_7$, $R_8$, and $R_9$ are the same or different and are independently selected from the group consisting of hydrogen, hydroxyalkyl of 1 to 5 carbons, hydroxy, alkyl or from 1 to 5 carbon atoms, halogen, haloalkyl of 1 to 5 carbon atoms, carboxy, alkylcarbonylalkyl of 2 to 10 carbons, alkanoyloxy of 1 to 5 carbon atoms, carboxyalkyl of 1 to 5 carbons atoms, acyl, amido, cyano, amidoalkyl of 1 to 5 carbons, N-monoalkylamidoalkyl of 2 to 10 carbons, N,N-dialkylamidoalkyl of 4 to 10 carbons, cyanoalkyl of 1 to 5 carbons alkoxy of 1 to 5 carbon atoms, alkoxyalkyl of 2 to 10 carbon atoms and —COR$_{10}$ wherein R$_{10}$ is alkyl of 1 to 5 carbons; and X is halogen; while the ammonium salt is illustrated, it is understood that other pharmaceutically acceptable salts such as K+ are within the scope of the invention. The compounds with the five membered rings are preferred.

As used herein and in the appended claims, the term alkyl of 1 to 5 carbon atoms includes straight and branched chain alkyl groups such as methyl; ethyl; n-propyl; n-butyl, and the like; the term hydroxyalkyl of 1 to 5 carbon atoms includes hydroxymethyl; hydroxyethyl; hydroxy-n-butyl; the term halkoakyl of 1 to 5 carbon atoms includes chloromethyl; 2-iodoethyl; 4-bromo-n-butyl; iodoethyl; 4-bromo-n-pentyl and the like; the term alkanoyloxy of 1 to 5 carbon atoms includes acetyl, propionyl, butanoyl and the like; the term carboxyalkyl includes carboxymethyl, carboxyethyl, ethylenecarboxy and the like; the term alkylcarbonylalkyl includes methanoylmethyl, ethanoylethyl and the like; the term amidoalkyl includes —CH$_2$CONH$_2$; —CH$_2$CH$_2$CONH$_2$; —CH$_2$CH$_2$CH$_2$CONH$_2$ and the like; the term cyanoalkyl includes —CH$_2$CN; —CH$_2$CH$_2$CN; —CH$_2$CH$_2$CH$_2$CN and the like; the alkoxy, of 1 to 5 carbon atoms includes methoxy, ethoxy, n-propoxy, n-pentoxy and the like; the terms halo and halogen are used to signify chloro, bromo, iodo and fluoro; the term acyl includes R$_{16}$CO wherein R$_{16}$ is H or alkyl of 1 to 5 carbons such as methanoyl, ethanoyl and the like; the term aryl includes phenyl, alkylphenyl and naphthyl; the term N-monoalkylamidoalkyl includes —CH$_2$CH$_2$CONHCH$_3$, —CH—$_2$CONHCH$_2$CH$_3$; the term N,N-dialkylamidoalkyl includes —CH$_2$CON(CH$_3$)$_2$; CH$_2$CH$_2$CON(CH$_2$—CH$_3$)$_2$. The tellurium based compounds that are preferred include those of the formula:

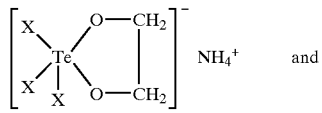 and

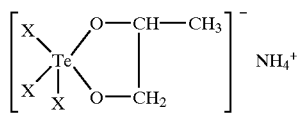

wherein X is halogen. The preferred halogen species is chloro.

Other compounds which are based on tellurium and may be used in the practice of the invention include PhTeCl$_3$, TeO$_2$ and TeX$_4$ (C$_6$H$_5$)$_4$ P+(TeCl$_3$(O$_2$C$_2$H$_4$))— (Z. Naturforsh, 36, 307–312 (1981). Compounds of the following structure are also included:

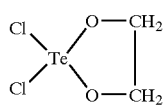

Other compounds useful for the practice of invention include:

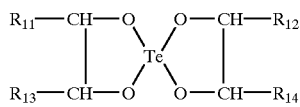

wherein R$_{11}$, R$_{12}$, R$_{13}$ and R$_{14}$ are independently selected from the group consisting of hydrogen, hydroxy-alkyl of 1–5 carbons atoms, hydroxy and alkyl of 1–5 carbons atoms.

Useful dihydroxy compounds for use in the preparation of compounds of structure A or B, include those of formula I wherein R, R$_1$, R$_4$ and R$_5$ are as shown in the Table:

TABLE (I)
HO—C(R)(R$_1$)—C(R$_4$)(R$_5$)—OH

| R | R$_1$ | R$_4$ | R$_5$ |
|---|---|---|---|
| H | H | H | H |
| H | Cl | H | H |
| H | OCH$_3$ | H | H |
| H | COOCH$_3$ | H | H |
| H | H | CN | H |
| H | CHO | H | H |
| H | H | COOH | H |
| H | CH$_2$COOH | H | H |
| H | H | CH$_2$COOCH$_3$ | H |
| H | I | H | H |
| H | H | Br | H |
| H | H | CONH$_2$ | H |

TABLE-continued (I)
HO—C(R)(R$_1$)—C(R$_4$)(R$_5$)—OH

| R | R$_1$ | R$_4$ | R$_5$ |
|---|---|---|---|
| H | H | CH$_2$OH | H |
| H | COOH | H | H |

Other dihydroxy compounds for use in the preparation of compounds A and B include those of formula II wherein R, R$_1$, R$_2$, R$_3$, R$_4$ and R$_5$ are as shown in the Table:

(II)
HO—C(R)(R$_1$)—C(R$_2$)(R$_3$)—C(R$_4$)(R$_5$)—OH

| R | R$_1$ | R$_2$ | R$_3$ | R$_4$ | R$_5$ |
|---|---|---|---|---|---|
| H | H | H | H | H | H |
| H | H | Cl | H | H | H |
| H | CH$_2$OH | H | H | H | H |
| H | H | OH | H | H | H |
| H | H | H | CH$_3$ | H | H |
| H | H | H | CH$_2$Cl | H | H |
| H | H | H | COOH | H | H |
| H | H | H | CH$_2$COOH | H | H |
| H | H | H | CHO | H | H |
| H | H | H | H | H | CH$_2$CHO |
| H | H | CONH$_2$ | H | H$_2$ | CH$_3$ |
| H | H | H | CN | H | H |
| H | H | H | H | CH$_2$COHN$_2$ | H |
| H | H | H | COOCH$_3$ | H$_3$ | H |
| H | H$_3$ | OCH$_3$ | H | H | H |

Other dihydroxy compounds for use in making compound of formula A and B include those of formula III wherein R, R$_1$, R$_2$, R$_3$, R$_4$ and R$_5$ are as shown in the Table.

(III)
HO—C(R)(R$_1$)—C(R$_2$)(R$_3$)—C(R$_4$)(R$_5$)—C(R$_8$)(R$_9$)—OH

| R | R$_1$ | R$_2$ | R$_3$ | R$_4$ | R$_5$ | R$_8$ | R$_9$ |
|---|---|---|---|---|---|---|---|
| H | H | H | H | H | H | H | H |
| H | H | Cl | H | H | H | H | H |
| H | H | H | H | Br | H | H | H |
| H | H | OCH$_3$ | H | H | H | H | H |
| H | H | CONH$_2$ | H | H | H | H | H |
| H | Br | H | H | H | H | H | H |
| H | H | H | H | CH$_2$COOH | H | H | H |
| H | H | Cl | Cl | H | H | H | H |
| H | CH$_2$COOH | H | H | H | H | H | H |
| H | H | CH$_3$ | H | H | H | H | H |
| H | CH$_3$ | H | H | H | H | H | H |
| H | CH$_2$Cl | H | H | H | H | H | H |
| H | H | H | I | H | H | H | H |
| H | CH$_2$CN | H | H | H | H | H | H |
| H | H | H | H | CH$_2$CH$_2$OH | H | H | H |

Additional dihydroxy compounds include those of formula IV wherein R, R$_1$, R$_2$, R$_3$, R$_4$ and R$_5$ are as shown in the Table.

(IV)

$$HO-\underset{\underset{R_1}{|}}{\overset{\overset{R}{|}}{C}}-\underset{\underset{R_3}{|}}{\overset{\overset{R_2}{|}}{C}}-\underset{\underset{R_5}{|}}{\overset{\overset{R_4}{|}}{C}}-\underset{\underset{R_7}{|}}{\overset{\overset{R_6}{|}}{C}}-\underset{R_9}{\overset{R_8}{|}}R-OH$$

| R | $R_1$ | $R_2$ | $R_3$ | $R_4$ | $R_5$ | $R_6$ | $R_7$ | $R_8$ | $R_9$ |
|---|---|---|---|---|---|---|---|---|---|
| H | H | H | H | H | H | H | H | H | H |
| H | H | Cl | H | H | H | Cl | H | H | H |
| H | H | Cl | Cl | H | H | H | H | H | H |
| H | H | $CONCH_3$ | H | H | H | Br | H | H | H |
| H | H | Br | H | H | H | $CON(CH_3)_2$ | H | H | H |
| H | H | H | $OCH_3$ | H | H | H | H | H | H |
| H | H | H | H | $OCH_3$ | H | H | H | H | H |
| H | H | H | H | $CH_2COOH$ | H | H | H | H | H |
| H | H | COOH | H | H | H | H | H | H | H |
| H | $CH_3$ | H | H | H | H | H | H | H | H |
| $CH_3$ | H | H | H | H | H | $CH_3$ | H | H | H |
| H | $CH_2CH_3$ | H | H | H | H | H | Cl | H | H |
| H | $CH_2CN$ | H | H | $CH_2OH$ | H | H | H | H | H |
| H | H | H | I | H | H | H | H | CN | H |
| H | $CH_2CH_2COOH$ | H | H | H | H | H | H | H | H |
| H | H | CHO | H | H | H | H | H | H | H |
| H | H | H | F | H | H | H | H | H | H |

Compounds of the following formula are also included:

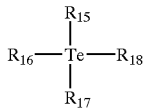

herein $R_{15}$, $R_{16}$, $R_{17}$ and $R_{18}$ are independently selected from halogen, alkyl of 1–5 carbons; aryl, acyl of 1–5 carbon hydroxyalkyl of 1–5 carbons and aminoalkyl of 1–5 carbons may be made by reacting the appropriate di, tri or tetrahalotelluride with the appropriate hydroxy compound which may be of the formula:

wherein $R_{19}$; is alkyl of 1 to 5 carbons, haloalkyl of 1 to 5 carbons, aryl, alkylaryl, alkylamido of 1 to 5 carbons, alkylcarbonyl of 1 to 5 carbons, cyanoalkyl of 1 to 5 carbons, cyanoalkyl of 1 to 5 carbons, and an alkoxyalkyl of 2 to 10 carbons. Specific examples of $R_{16}$ include methyl, ethyl, n-propyl, phenyl, tolyl, amidoethyl, cyanomethyl, methyloxymethyl and $CH_2CH_2COOH$.

These compounds are described in U.S. Pat. No. 4,761, 490 which is incorporated by reference. In addition, $TeCl_4$; $TeBr_4$ and compounds which give in aqueous solution $TeO_2$ preferably in the form of a complex such as for example $TeO_2$ complex with citric acid or ethylene glycol.

The preferred compound is ammonium trichloro (dioxoethylene-O,O') tellurate. The tellurium compound may be administered by orally or by parenteral injection into the of from 0.001 to 3 mg of the tellurium compound in a suitable aqueous vehicle once daily or in divided doses two to four times a day. The parenteral route of administration may be intravenously, subcutaneously, intramuscularly etc. The oral administration may be as a solid dosage form i.e. tablet with conventional excipients such as lactose, microcrystalline cellulose and the like or as as a solution i.e. 0.1%–0.3% in water, propylene glycol or any other non-toxic pharmaceutically acceptable liquid.

The preferred manner of administration is by topical administration where the tellurium compound is dispersed in a suitable vehicle at a concentration of 0.01 to 10% or more preferably from 0.1 to 5% by weight based on the total weight of the tellurium compound and the vehicle. The vehicle may be an aqueous solution or any organic liquid which is non-toxic and non-irritating to the skin. Examples of organic liquids include hydroalcoholic mixtures of water and ethanol, mixtures of propylene glycol and water, dimethyl sulfoxide and the like. Generally the water:organic solvent mixture will comprise 10:90 to 90:10 water:organic solvent. Hydrophillic or hydrophobic ointment bases (e.g. petrolatum) may also be used as the vehicle.

The tellurium compound may be employed alone as the sole active agent or in combination with a keratolytic agent. Any suitable keratolytic agent may be employed at a concentration which enhances the effect of the tellurium compound. The preferred keratolytic agent is salicylic acid. Generally the concentration of the keratolytic agent will be from 0.5 to 40% or more preferably from 1 to 20% by weight based on the weight of all of the components. The use of a keratolytic agent facilitates the penetration of the tellurium compound in to the skin in affected areas.

The efficacy of the invention has been demonstrated in the treatment of an adult female who has been afflicted with psoriasis for 15 years. The treatment was based on the application to the affected area (elbow) a solution of 1% by weight of ammonium trichloro (dioxoethylene O,O') tellurate and 10% by weight of salicylic acid in propylene glycol (all weights are based on the total weight of the composition). The solution was applied to the affected area twice a day for three days. Thereafter, the treated area turned black and crusty. After several days the black crust gradually faded and the skin return ed to a normal color and appearance. The elapsed time was 10 days from the initiation of treatment.

A second test was carried out using 2% by weight of ammonium trichloro (dioxoethylene-O,O') tellurate and 5% by weight of salicylic acid in dimethyl sulfoxide (all weights are based on the total weight of the composition). The skin did not change color and after 3 days the affected area returned to a normal appearance.

The best results are obtained by using a concentration of 2% by weight of ammonium trichloro (dioxoethylene-O,O') tellurate and 5% by weight of salicylic acid in petrolatum applied two to three times a day to the affected area for three to five days followed by a second course of therapy using 1% by weight of ammonium trichloro (dioxoethylene-O,O') tellurate and 1% by weight of salicylic acid in petrolatum applied two to three times a day times daily for three to five days followed by a third course of therapy using 1% by weight of ammonium trichloro (dioxoethylene-O,O') tellurate alone in petrolatum which was applied to the affected area two to three times daily for two to seven days. All percents by weight are based on the total weight of the particular composition.

Separate tests showed that ammonium trichloro (dioxoethylene-O,O') tellurate was effective for treating psoriasis but worked very slowly. Salicylic acid alone was ineffective.

The foregoing description of a preferred embodiment of the invention has been presented for purposes of illustration and description. It is not intended to be exhaustive or to limit the invention to the precise form disclosed. Obvious modifications or variations are possible in light of the above teachings. All such obvious modifications and variations are intended to be within the scope of the appended claims.

We claim:

1. A method for treating psoriasis which comprises administering to an affected patient an effective amount of a compound of the formula:

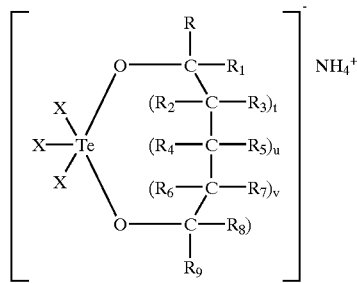

(A)

or the complex of $TeO_2 \cdot HOCH_2CH_2 \cdot NH_4Cl$;

or

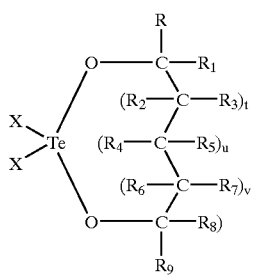

(B)

or $TeO_2$ or complexes of $TeO_2$ or $PhTeCl_3$ (D)

or

$(C_6H_5)_4P^+(TeCl_3(O_2C_2H_4))^- \cdot TeX_4$, wherein t is 1 or 0; u is 1 or 0; v is 1 or 0; R, $R_1$, $R_2$, $R_3$, $R_4$, $R_5$, $R_6$, $R_7$, $R_8$, and $R_9$ are the same or different and are independently selected from the group consisting of hydrogen, hydroxyalkyl of 1 to 5 carbons, hydroxy, alkyl of 1 to 5 carbon atoms, halogen, haloalkyl of 1 to 5 carbon atoms, carboxy, alkylcarbonylalkyl of 2 to 10 carbons, alkanoyloxy of 1 to 5 carbon atoms, carboxyalkyl of 1 to 5 carbons atoms, acyl, amido, cyano, amidoalkyl of 1 to 5 carbons, N-monoalkylamidoalkyl of 2 to 10 carbons, N,N-dialkylamidoalkyl of 4 to 10 carbons, cyanoalkyl of 1 to 5 carbons alkoxy of 1 to 5 carbon atoms, alkoxyalkyl of 2 to 10 carbon atoms and —$COR_{10}$ wherein $R_{10}$, is alkyl of from 1 to 5 carbons; and X is halogen and complexes thereof.

2. A method as defined in claim 1 wherein the compound is a tellurium compound which is ammonium trichloro (dioxoethyelene-O,O') tellurate.

3. A method as defined in claim 1 wherein the compound is administered parenterally.

4. A method as defined in claim 1 wherein the compound is administered orally.

5. A method as defined in claim 1 wherein the compound is administered topically.

6. A method as defined in claim 5 wherein the compound is administered in combination with a keratolytic agent.

7. A method as defined in claim 6 wherein the keratolytic agent is salicylic acid.

8. A topical composition for treating psoriasis which comprises an effective amount of a compound of the formula:

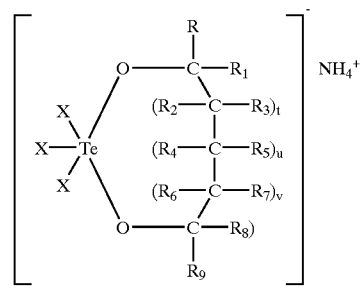

(A)

or the complex of $TeO_2 \cdot HOCH_2CH_2 \cdot NH_4Cl$;

or

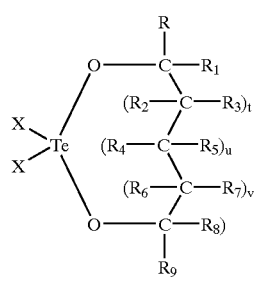

(B)

or $TeO_2$ or complexes of $TeO_2$ or

PhTeCl₃ (D)

or (C₆H₅)₄P+(TeCl₃(O₂C₂H₄))−TeX₄, wherein t is 1 or 0; u is 1 or 0; v is 1 or 0; R, $R_1$, $R_2$, $R_3$, $R_4$, $R_5$, $R_6$, $R_7$, $R_8$, and $R_9$ are the same or different and are independently selected from the group consisting of hydrogen, hydroxyalkyl of 1 to 5 carbons, hydroxy, alkyl of 1 to 5 carbon atoms, halogen, haloalkyl of 1 to 5 carbon atoms, carboxy, alkylcarbonylalkyl of 2 to 10 carbons, alkanoyloxy of 1 to 5 carbon atoms, carboxyalkyl of 1 to 5 carbons atoms, acyl, amido, cyano, amidoalkyl of 1 to 5 carbons, N-monoalkylamidoalkyl of 2 to 10 carbons, N,N-dialkylamidoalkyl of 4 to 10 carbons, cyanoalkyl of 1 to 5 carbons alkoxy of 1 to 5 carbon atoms, alkoxyalkyl of 2 to 10 carbon atoms and —$COR_{10}$ wherein $R_{10}$ is alkyl of from 1 to 5 carbons; and X is halogen and complexes thereof and a keratolytic agent.

9. A topical composition for treating psoriasis as which comprises an effective amount of a compound of the formula:

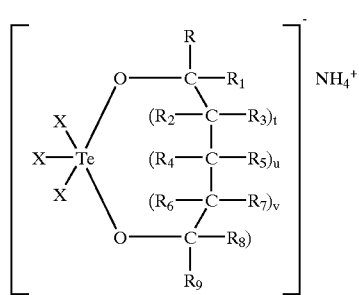
(A)

or the complex of TeO₂.HOCH₂CH₂.NH₄Cl;

or

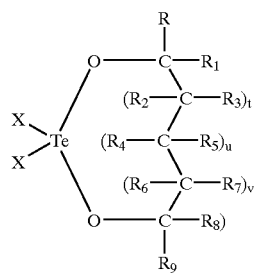
(B)

or

TeO₂ or complexes of TeO₂ or

PhTeCl₃ (D)

or (C₆H₅)₄P+(TeCl₃(O₂C₂H₄))−TeX₄, wherein t is 1 or 0; u is 1 or 0; v is 1 or 0; R, $R_1$, $R_2$, $R_3$, $R_4$, $R_5$, $R_6$, $R_7$, $R_8$, and $R_9$ are the same or different and are independently selected from the group consisting of hydrogen, hydroxyalkyl of 1 to 5 carbons, hydroxy, alkyl of 1 to 5 carbon atoms, halogen, haloalkyl of 1 to 5 carbon atoms, carboxy, alkylcarbonylalkyl of 2 to 10 carbons, alkanoyloxy of 1 to 5 carbon atoms, carboxyalkyl of 1 to 5 carbons atoms, acyl, amido, cyano, amidoalkyl of 1 to 5 carbons, N-monoalkylamidoalkyl of 2 to 10 carbons, N,N-dialkylamidoalkyl of 4 to 10 carbons, cyanoalkyl of 1 to 5 carbons alkoxy of 1 to 5 carbon atoms, alkoxyalkyl of 2 to 10 carbon atoms and —$COR_{10}$ wherein $R_{10}$ is alkyl of from 1 to 5 carbons; and X is halogen and complexes thereof and salicylic acid.

10. A topical composition for treating psoriasis as which comprises an effective amount of ammonium trichloro (dioxoethyelene-O,O') tellurate and salicylic acid.

* * * * *